(12) United States Patent
von Oepen et al.

(10) Patent No.: US 10,639,151 B2
(45) Date of Patent: May 5, 2020

(54) THREADED COIL

(71) Applicant: Cephea Valve Technologies, Inc., Santa Clara, CA (US)

(72) Inventors: Randolf von Oepen, Aptos, CA (US); Sean A. McNiven, Menlo Park, CA (US)

(73) Assignee: Cephea Valve Technologies, Inc., Santa Clara, CA (US)

(*) Notice: Subject to any disclaimer, the term of this patent is extended or adjusted under 35 U.S.C. 154(b) by 181 days.

(21) Appl. No.: 15/662,001

(22) Filed: Jul. 27, 2017

(65) Prior Publication Data

US 2018/0028305 A1 Feb. 1, 2018

Related U.S. Application Data

(60) Provisional application No. 62/368,695, filed on Jul. 29, 2016.

(51) Int. Cl.
*A61F 2/24* (2006.01)
*A61B 17/00* (2006.01)
*A61F 2/95* (2013.01)
*F16B 37/00* (2006.01)
*A61F 2/01* (2006.01)

(52) U.S. Cl.
CPC .............. *A61F 2/2436* (2013.01); *A61F 2/95* (2013.01); *A61F 2/2427* (2013.01); *A61F 2/2466* (2013.01); *A61F 2002/011* (2013.01); *A61F 2002/016* (2013.01); *A61F 2230/0091* (2013.01); *F16B 37/00* (2013.01)

(58) Field of Classification Search
CPC ........ A61F 2/95; A61F 2/2436; A61F 2/2427; A61F 2002/011; A61F 2002/016; A61F 2230/0091; A61F 2/2466; F16B 37/00
See application file for complete search history.

(56) References Cited

U.S. PATENT DOCUMENTS

| | | | |
|---|---|---|---|
| 4,406,656 A | 9/1983 | Hattler et al. |
| 4,728,319 A | 3/1988 | Masch |
| 5,053,043 A | 10/1991 | Gottesman et al. |
| 5,059,213 A | 10/1991 | Chesterfield et al. |

(Continued)

FOREIGN PATENT DOCUMENTS

| | | |
|---|---|---|
| CN | 1469724 | 1/2004 |
| CN | 102770080 | 11/2012 |

(Continued)

OTHER PUBLICATIONS

Hironobu Takizawa et al. "Development of a Microfine Active Bending Catheter Equipped with Mif Tactile Sensors", Micro Electro Mechanical Systems, IEEE, Jan. 17, 1999, pp. 412-417.

(Continued)

*Primary Examiner* — Julian W Woo
(74) *Attorney, Agent, or Firm* — Workman Nydegger (57) ABSTRACT

An intravascular delivery system includes a threaded coil. The threaded coil includes one or more wires coiled to form a spiral coil with at least one thread extending along a length of the threaded coil. The threaded coil is elastically deformable for delivery of the threaded coil to a target location in the body and is rotatable to longitudinally position an intravascular device at the target location.

18 Claims, 5 Drawing Sheets

(56) References Cited

U.S. PATENT DOCUMENTS

| | | | |
|---|---|---|---|
| 5,078,722 A * | 1/1992 | Stevens | A61B 17/320783 604/22 |
| 5,078,723 A * | 1/1992 | Dance | A61B 17/3207 604/22 |
| 5,236,450 A | 8/1993 | Scott | |
| 5,325,845 A | 7/1994 | Adair | |
| 5,345,945 A * | 9/1994 | Hodgson | A61M 25/09033 600/433 |
| 5,387,219 A | 2/1995 | Rappe | |
| 5,415,664 A | 5/1995 | Pinchuk | |
| 5,472,423 A | 12/1995 | Gronauer | |
| 5,571,085 A | 11/1996 | Accisano | |
| 5,662,606 A | 9/1997 | Cimino et al. | |
| 5,669,919 A | 9/1997 | Sanders et al. | |
| 5,769,812 A | 6/1998 | Stevens et al. | |
| 5,807,405 A | 9/1998 | Vanney et al. | |
| 5,820,591 A | 10/1998 | Thompson et al. | |
| 5,843,103 A * | 12/1998 | Wulfman | A61B 17/320758 606/159 |
| 5,855,601 A | 1/1999 | Bessler et al. | |
| 5,873,882 A | 2/1999 | Straub et al. | |
| 5,902,334 A | 5/1999 | Dwyer et al. | |
| 5,906,642 A | 5/1999 | Caudillo et al. | |
| 5,957,973 A | 9/1999 | Quiachon et al. | |
| 6,090,118 A * | 7/2000 | McGuckin, Jr. | A61B 17/22 606/159 |
| 6,180,059 B1 | 1/2001 | Divino, Jr. et al. | |
| 6,228,110 B1 | 5/2001 | Munsinger | |
| 6,458,137 B1 | 10/2002 | Klint | |
| 6,517,550 B1 | 2/2003 | Konya et al. | |
| 6,695,836 B1 | 2/2004 | Demello et al. | |
| 6,926,725 B2 * | 8/2005 | Cooke | A61B 17/320758 606/159 |
| 7,172,617 B2 | 2/2007 | Colgan et al. | |
| 7,344,553 B2 | 3/2008 | Opolski et al. | |
| 7,666,204 B2 | 2/2010 | Thornton et al. | |
| 7,736,388 B2 | 6/2010 | Goldfarb et al. | |
| 7,837,727 B2 | 11/2010 | Goetz et al. | |
| 7,988,724 B2 | 8/2011 | Salahieh et al. | |
| 7,993,303 B2 | 8/2011 | Von Oepen et al. | |
| 8,157,852 B2 | 4/2012 | Bloom et al. | |
| 8,523,881 B2 * | 9/2013 | Cabin; Oz | A61B 17/064 606/139 |
| 8,647,323 B2 | 2/2014 | Guo et al. | |
| 8,911,455 B2 | 12/2014 | Quadri et al. | |
| 8,926,588 B2 | 1/2015 | Berthiaume et al. | |
| 8,926,692 B2 | 1/2015 | Dwork | |
| 9,339,378 B2 | 5/2016 | Quadri et al. | |
| 9,370,423 B2 | 6/2016 | Ryan | |
| 9,393,112 B2 | 7/2016 | Tuval et al. | |
| 9,399,112 B2 | 7/2016 | Shevgoor et al. | |
| 9,668,859 B2 | 6/2017 | Kheradvar et al. | |
| 9,687,373 B2 | 6/2017 | Vad | |
| 9,693,862 B2 | 7/2017 | Campbell et al. | |
| 9,801,745 B2 | 10/2017 | Wubbeling et al. | |
| 10,111,671 B2 * | 10/2018 | Bodewadt | A61B 17/1214 |
| 10,117,760 B2 * | 11/2018 | Mangiardi | A61F 2/82 |
| 10,376,673 B2 | 8/2019 | Van Hoven et al. | |
| 10,398,553 B2 | 9/2019 | Kizuka | |
| 10,470,902 B2 * | 11/2019 | Sheldon | B23K 26/20 |
| 2001/0002445 A1 | 5/2001 | Vesely | |
| 2002/0013547 A1 | 1/2002 | Paskar | |
| 2004/0049207 A1 | 3/2004 | Goldfarb et al. | |
| 2004/0116848 A1 | 6/2004 | Gardeski et al. | |
| 2004/0127849 A1 | 7/2004 | Kantor | |
| 2004/0133232 A1 | 7/2004 | Rosenbluth et al. | |
| 2004/0147826 A1 | 7/2004 | Peterson | |
| 2005/0038383 A1 | 2/2005 | Kelley et al. | |
| 2005/0085903 A1 | 4/2005 | Lau | |
| 2005/0137695 A1 | 6/2005 | Salahieh et al. | |
| 2005/0143809 A1 | 6/2005 | Salahieh et al. | |
| 2005/0256452 A1 | 11/2005 | Demarchi et al. | |
| 2005/0283231 A1 | 11/2005 | Haug et al. | |
| 2005/0277874 A1 | 12/2005 | Selkee | |
| 2005/0277876 A1 | 12/2005 | Hayden | |
| 2006/0135961 A1 | 6/2006 | Rosenman et al. | |
| 2007/0060997 A1 | 3/2007 | De Boer | |
| 2007/0156225 A1 | 7/2007 | George et al. | |
| 2007/0173757 A1 | 7/2007 | Levine et al. | |
| 2007/0197858 A1 | 8/2007 | Goldfarb et al. | |
| 2007/0203561 A1 | 8/2007 | Forster et al. | |
| 2007/0260225 A1 | 11/2007 | Sakakine et al. | |
| 2007/0299424 A1 | 12/2007 | Cumming et al. | |
| 2008/0103585 A1 * | 5/2008 | Monstadt | A61B 17/12022 623/1.22 |
| 2008/0188850 A1 | 8/2008 | Mody et al. | |
| 2008/0195126 A1 | 8/2008 | Solem | |
| 2009/0036768 A1 | 2/2009 | Seehusen et al. | |
| 2009/0099554 A1 | 4/2009 | Forster et al. | |
| 2009/0163934 A1 | 6/2009 | Raschdorf, Jr. et al. | |
| 2009/0204005 A1 | 8/2009 | Keast et al. | |
| 2009/0240326 A1 | 9/2009 | Wilson et al. | |
| 2009/0276039 A1 | 11/2009 | Meretei | |
| 2009/0281619 A1 | 11/2009 | Le et al. | |
| 2010/0004739 A1 | 1/2010 | Vesely | |
| 2010/0044410 A1 | 2/2010 | Argentine et al. | |
| 2010/0217261 A1 | 8/2010 | Watson | |
| 2010/0249894 A1 | 9/2010 | Oba et al. | |
| 2010/0331776 A1 | 12/2010 | Salahieh et al. | |
| 2011/0112630 A1 | 5/2011 | Groothuis et al. | |
| 2011/0166566 A1 | 7/2011 | Gabriel | |
| 2011/0257718 A1 | 10/2011 | Argentine | |
| 2011/0307049 A1 | 12/2011 | Kao | |
| 2012/0022640 A1 | 1/2012 | Gross et al. | |
| 2012/0065464 A1 | 3/2012 | Ellis et al. | |
| 2012/0109078 A1 | 5/2012 | Schaeffer | |
| 2012/0172915 A1 | 7/2012 | Fifer et al. | |
| 2012/0316639 A1 | 12/2012 | Kleinschrodt | |
| 2012/0330348 A1 | 12/2012 | Strauss et al. | |
| 2012/0330408 A1 | 12/2012 | Hillukka et al. | |
| 2013/0041314 A1 | 2/2013 | Dillon | |
| 2013/0066342 A1 | 3/2013 | Dell et al. | |
| 2013/0103001 A1 | 4/2013 | Benmaamer et al. | |
| 2013/0131775 A1 | 5/2013 | Hadley et al. | |
| 2014/0107693 A1 | 4/2014 | Plassman | |
| 2014/0148889 A1 | 5/2014 | Deshmukh et al. | |
| 2014/0180124 A1 | 6/2014 | Vvhiseant et al. | |
| 2014/0228871 A1 | 8/2014 | Cohen et al. | |
| 2014/0276966 A1 | 9/2014 | Ranucci et al. | |
| 2014/0324164 A1 | 10/2014 | Gross et al. | |
| 2014/0379074 A1 | 12/2014 | Spence et al. | |
| 2015/0005704 A1 | 1/2015 | Heisel et al. | |
| 2015/0005801 A1 | 1/2015 | Marquis et al. | |
| 2015/0088189 A1 | 3/2015 | Paul, Jr. | |
| 2015/0112430 A1 | 4/2015 | Creaven et al. | |
| 2015/0272759 A1 | 10/2015 | Argentine | |
| 2015/0306806 A1 | 10/2015 | Dando et al. | |
| 2016/0045311 A1 | 2/2016 | McCann et al. | |
| 2017/0035566 A1 | 2/2017 | Krone et al. | |
| 2017/0042678 A1 | 2/2017 | Ganesan et al. | |
| 2017/0080186 A1 | 3/2017 | Salahieh et al. | |
| 2017/0232238 A1 | 8/2017 | Biller et al. | |
| 2018/0028177 A1 | 2/2018 | von Oepen et al. | |
| 2018/0028215 A1 | 2/2018 | Cohen | |
| 2018/0028779 A1 | 2/2018 | von Oepen et al. | |
| 2018/0028787 A1 | 2/2018 | McNiven et al. | |
| 2018/0055636 A1 | 3/2018 | Valencia et al. | |
| 2018/0055637 A1 | 3/2018 | von Oepen et al. | |
| 2018/0056033 A1 | 3/2018 | von Oepen et al. | |
| 2018/0056043 A1 | 3/2018 | von Oepen et al. | |
| 2018/0092744 A1 | 4/2018 | von Oepen et al. | |
| 2018/0126119 A1 | 5/2018 | McNiven et al. | |
| 2018/0133454 A1 | 5/2018 | von Oepen et al. | |
| 2018/0360457 A1 | 12/2018 | Ellis et al. | |
| 2019/0030285 A1 | 1/2019 | Prabhu et al. | |
| 2019/0274831 A1 | 9/2019 | Prabhu | |

FOREIGN PATENT DOCUMENTS

| | | |
|---|---|---|
| CN | 103841899 | 6/2014 |
| EP | 1980288 | 10/2008 |
| EP | 2537487 | 12/2012 |
| EP | 2702965 | 3/2014 |

(56) References Cited

FOREIGN PATENT DOCUMENTS

| | | |
|---|---|---|
| EP | 3009103 | 4/2016 |
| JP | 2003062072 | 3/2003 |
| JP | 2006528911 | 12/2006 |
| JP | 2013516244 | 5/2013 |
| WO | WO 2001051114 | 7/2001 |
| WO | WO 2007044285 | 4/2007 |
| WO | WO 2007136829 | 11/2007 |
| WO | WO 2008103722 | 8/2008 |
| WO | WO 2010024801 | 3/2010 |
| WO | WO 2010121076 | 10/2010 |
| WO | WO 2012020521 | 2/2012 |
| WO | WO 2012151396 | 11/2012 |
| WO | WO 2014064694 | 5/2014 |
| WO | WO 2014121280 | 8/2014 |
| WO | WO 2014128705 | 8/2014 |
| WO | WO 2015191938 | 12/2015 |
| WO | WO 2016022797 | 2/2016 |
| WO | WO 2016112085 | 7/2016 |
| WO | WO 2016144708 | 9/2016 |
| WO | WO 2016150806 | 9/2016 |
| WO | WO 2016183526 | 11/2016 |
| WO | WO 2018023038 | 2/2018 |
| WO | WO 2018023043 | 2/2018 |
| WO | WO 2018023044 | 2/2018 |
| WO | WO 2018023045 | 2/2018 |
| WO | WO 2018023052 | 2/2018 |
| WO | WO 2018044446 | 3/2018 |
| WO | WO 2018044447 | 3/2018 |
| WO | WO 2018044448 | 3/2018 |
| WO | WO 2018044449 | 3/2018 |
| WO | WO 2018067788 | 4/2018 |

OTHER PUBLICATIONS

U.S. Appl. No. 15/662,013, dated Jun. 13, 2019, Office Action.
U.S. Appl. No. 15/662,013, dated Oct. 10, 2019, Office Action.
U.S. Appl. No. 15/662,013, dated Dec. 5, 2019, Advisory Action.
U.S. Appl. No. 15/662,066, dated Jul. 11, 2019, Office Action.
U.S. Appl. No. 15/662,066, dated Dec. 16, 2019, Office Action.
U.S. Appl. No. 15/662,066, dated Feb. 27, 2020, Advisory Action.
U.S. Appl. No. 15/662,142, Dec. 20, 2019, Advisory Action.
U.S. Appl. No. 15/662,076 dated Oct. 8, 2019, Notice of Allowance.
U.S. Appl. No. 15/662,076, dated Jan. 31, 2020, Notice of Allowance.
U.S. Appl. No. 15/662,089, dated Oct. 7, 2019, Office Action.
U.S. Appl. No. 15/662,089, dated Jan. 10, 2020, Office Action.
U.S. Appl. No. 15/662,093, dated Mar. 7, 2019, Office Action.
U.S. Appl. No. 15/662,093, dated Aug. 29, 2019, Office Action.
U.S. Appl. No. 15/662,093, dated Dec. 3, 2019, Office Action.
U.S. Appl. No. 15/662,008, dated Sep. 13, 2019, Office Action.
U.S. Appl. No. 15/662,008, dated Jan. 31, 2020, Notice of Allowance.
U.S. Appl. No. 15/662,098, dated Jul. 5, 2019, Office Action.
U.S. Appl. No. 15/662,098, dated Jan. 27, 2020, Office Action.
U.S. Appl. No. 15/724,499, dated Jul. 15, 2019, Notice of Allowance.
U.S. Appl. No. 15/724,499, dated Aug. 27, 2019, Supplemental Notice of Allowance.
U.S. Appl. No. 15/724,499, dated Nov. 22, 2019, Supplemental Notice of Allowance.

* cited by examiner

THREADED COIL

CROSS-REFERENCE TO RELATED APPLICATIONS

This application, which claims priority to U.S. Provisional Patent Application No. 62/368,695, filed Jul. 29, 2016, the entire contents of which are incorporated by reference herein.

BACKGROUND OF THE DISCLOSURE

Intravascular medical procedures allow the performance of therapeutic treatments in a variety of locations within a patient's body while requiring only relatively small access incisions. An intravascular procedure may, for example, eliminate the need for open-heart surgery, thereby reducing the risks, costs, and time associated with an open-heart procedure. The intravascular procedure also enables faster recovery times with lower associated costs and risks of complication. An example of an intravascular procedure which significantly reduces procedure and recovery time and cost over conventional open surgery is a heart valve replacement or repair procedure. An artificial valve is guided to the heart through the patient's vasculature. For example, a catheter is inserted into the patient's vasculature and directed to the inferior vena cava. The catheter is then urged through the inferior vena cava toward the heart by applying force longitudinally to the catheter. Upon entering the heart from the inferior vena cava, the catheter enters the right atrium. The distal end of the catheter may be deflected by one or more wires positioned inside the catheter. Precise control of the distal end of the catheter allows for more reliable and faster positioning of a medical device and/or implant and other improvements in the procedures.

An intravascularly delivered device needs to be placed precisely, as the device may be difficult to reposition after the device is fully deployed from the delivery system. Additionally, the ability to recapture and/or reposition a partially deployed device is desirable in the event that the distal end of the catheter moves relative to the target location and compromises the precise positioning of the device.

The precise positioning of the device is inhibited by controlling the movement of the device from the proximal end of the delivery system. An intravascular device delivery system can include an elongated body which is 75 centimeters or more in length within the patient's vasculature. Small movements, either longitudinally or rotationally, are limited by contact with the vasculature as the elongated body passed through the vasculature and around corners. Further, the internal friction of different layers and/or components of the intravascular device delivery system impairs the implementation of small movements by a medical profession or other user.

BRIEF SUMMARY OF THE DISCLOSURE

In an embodiment, a threaded device includes at least one elastically deformable wire spiraled about a longitudinal axis. The at least one elastically deformable coil defines a lumen through the device and has at least one thread on a radially outer surface.

In another embodiment, an intravascular device delivery system includes an elongated member, a threaded coil positioned in the elongated body, and a drive cable positioned in the elongated member and rotationally fixed to the threaded coil. The elongated member has a proximal end, a distal end, and a longitudinal axis therebetween. The threaded coil is positioned near the distal end of the elongated member and includes at least one elastically deformable wire spiraled about a longitudinal axis. The at least one elastically deformable coil defines a lumen through the device and has at least one thread on a radially outer surface.

A method of delivering an intravascular device includes inserting an elongated body containing a threaded coil and a distal end cap into a patient's vasculature. The intravascular device is positioned at the distal end of the elongated body. The method further includes applying a rotational force to the threaded coil, engaging a thread of the threaded coil with a complimentary thread; and rotating the threaded coil to apply a longitudinal force between the complimentary thread and the threaded coil.

This summary is provided to introduce a selection of concepts that are further described below in the detailed description. This summary is not intended to identify specific features of the claimed subject matter, nor is it intended to be used as an aid in limiting the scope of the claimed subject matter.

Additional features of embodiments of the disclosure will be set forth in the description which follows. The features of such embodiments may be realized by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which:

FIG. 3-1 is a side cross-sectional view of the distal end of the elongated member of the embodiment of an intravascular device delivery system of FIG. 1 showing distal movement of an intravascular device, according to the present disclosure;

FIG. 3-2 is a side cross-sectional view of the distal end of the elongated member of the embodiment of an intravascular device delivery system of FIG. 1 showing proximal movement of an intravascular device, according to the present disclosure;

FIG. 4-1 is a side cross-sectional view of the distal end of the elongated member of another embodiment of an intravascular device delivery system showing proximal movement of an outer sheath, according to the present disclosure;

FIG. 4-2 is a side cross-sectional view of the distal end of the elongated member of the embodiment of an intravascular device delivery system of FIG. 4-1 and showing distal movement of an outer sheath, according to the present disclosure;

DETAILED DESCRIPTION

One or more specific embodiments of the present disclosure will be described below. In an effort to provide a concise description of these embodiments, some features of an actual embodiment may be described in the specification. It should be appreciated that in the development of any such actual embodiment, as in any engineering or design project, numerous embodiment-specific decisions will be made to achieve the developers' specific goals, such as compliance with system-related and business-related constraints, which may vary from one embodiment to another. It should further be appreciated that such a development effort might be complex and time consuming, but would nevertheless be a routine undertaking of design, fabrication, and manufacture for those of ordinary skill having the benefit of this disclosure.

One or more embodiments of the present disclosure may generally relate to manufacturing and using intravascular device delivery systems or other steerable intravascular system. An intravascular device delivery system may allow a medical professional to deliver an intravascular or other medical device to a target location in a patient's body. While the present disclosure will describe intravascular device delivery systems and applications thereof in relation to intravascular procedures in the heart, it should be understood that the devices, systems, and method described herein may be applicable to other bodily lumens and/or cavities. Additionally, elements described in relation to any embodiment depicted and/or described herein may be combinable with elements described in relation to any other embodiment depicted and/or described herein. For example, any element described in relation to an embodiment depicted in FIG. 3-1 may be combinable with any element of an embodiment described in FIG. 10, and any element described in relation to an embodiment described in FIG. 4-2 may be combinable with any element of an embodiment depicted in FIG. 8.

An intravascular device delivery system may include a flexible elongated member that has a distal end and a proximal end. A handle may be connected to a proximal end of the elongated member to allow a user, such as a medical professional and/or clinician, to control one or more movements of the elongated member. An intravascular device may be positioned at and/or connected to the distal end of the elongated member.

In some embodiments, the elongated member may include a plurality of elements. For example, the elongated member may include a plurality of elements that extend from the proximal end to the distal end. In some embodiments, at least one of the elements of the elongated member may be located radially about a drive cable. In at least one embodiment, at least one element of the elongated member is located coaxially with and around a drive cable.

In some embodiments, the handle may include one or more controls (e.g., a knob, a button, a lever, or other controls) that may move at least one part of the intravascular device delivery system relative to another. For example, the handle may include one or more controls for moving at least one element of the elongated member relative to another element of the elongated member. The handle may move an inner element relative to an outer element of the elongated member in a proximal direction, in a distal direction, in a rotational direction, or combinations thereof.

Figure 1:
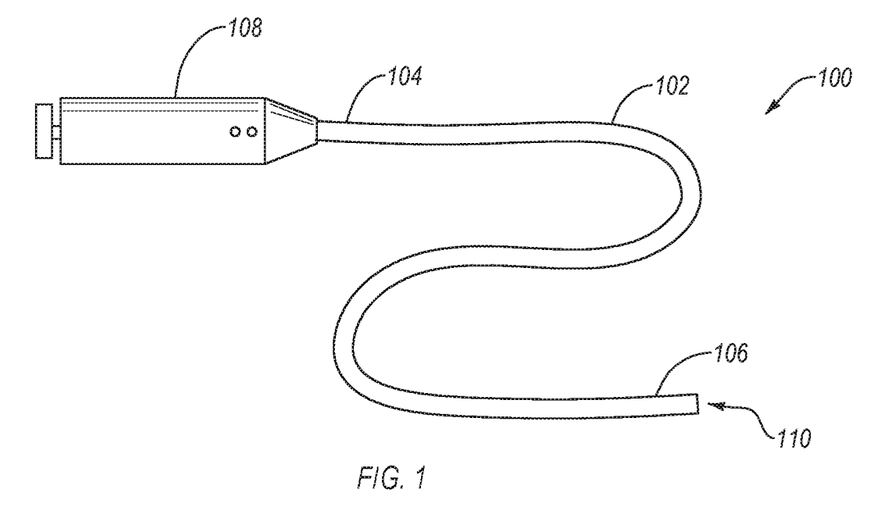
FIG. 1 is a schematic representation of an embodiment of an intravascular device delivery system, according to the present disclosure.

FIG. 1 illustrates a schematic representation of an intravascular device delivery system 100. The system 100 may include an elongated member 102 having a proximal end 104 and a distal end 106. A handle 108 may be connected to the proximal end 104 of the elongated member 102. An intravascular device 110 may be positioned at and/or connected to the distal end 106.

The elongated member 102 may be flexible, allowing the elongated member 102 to traverse a patient's tortuous vasculature or other anatomy. In some embodiments, the elongated member 102 may deliver the intravascular device 110 (not visible) to a target location in the patient's body, such as delivering a heart valve repair device to the heart. In other embodiments, the system 100 and elongated member 102 may be provided without an intravascular device 110 at the distal end 106 such that the system may recapture, reposition, or otherwise move an intravascular device previously positioned in the patient's body.

The elongated member 102 of the system 100 may include one or more elements therein. An element of the elongated member 102 may include a catheter, a guidewire, a sheath, a drive cable, other tubular and/or solid elements, or combinations thereof. In some embodiments, an element of the elongated member 102 may extend the entire length of the elongated member 102 from a proximal end 104 to a distal end 106 of the elongated member 102. In other embodiments, an element of the elongated member 102 may have a length less than the entire length of the elongated member 102. For example, an element may provide support to the elongated member 102 from the proximal end 104 toward the distal end 106 without continuing the entire length to the distal end 106.

Figure 2:
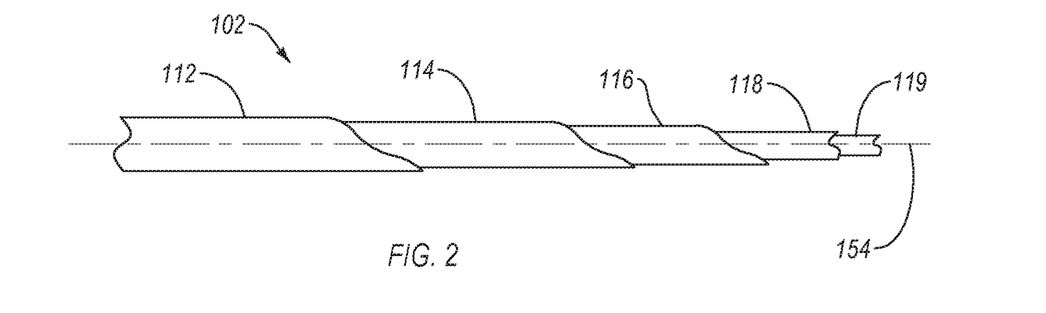
FIG. 2 is a side cutaway detail view of the elongated member of the embodiment of an intravascular device delivery system of FIG. 1, according to the present disclosure.

FIG. 2 is a side cutaway detail view of an embodiment of an elongated member 102 having a plurality of elements positioned radially within one another. For example, an elongated member 102 may have outer sheath 112 with one or more elements positioned radially within the outer sheath 112. In some embodiments, the outer sheath 112 may be an outermost element of the elongated member 102. In other embodiments, at least part of the outer sheath 112 may be within an outermost element of the elongated member 102.

In some embodiments, an elongated member 102 may have a delivery catheter 114 positioned radially within the outer sheath 112. For example, at least a portion of the delivery catheter 114 may longitudinally overlap with a portion of the outer sheath 112 and the delivery catheter 114 may be within a lumen or other cavity of the outer sheath 112. In other embodiments, the outer sheath 112 may have a plurality of elements positioned radially within the outer sheath 112. For example, the delivery catheter 114 and an inner catheter 116 may be positioned radially within the outer sheath 112. For example, both the delivery catheter 114 and inner catheter 116 may be radially within the outer sheath 112 and radially adjacent one another. In another example, the inner catheter 116 may be radially within the delivery catheter 114 and both may be radially within the outer sheath 112. In yet other embodiments, the outer sheath 112 may have the delivery catheter 114, the inner catheter 116, and a drive cable 118 radially within the outer sheath 112, as shown in FIG. 2.

In some embodiments, the outer sheath 112 and the delivery catheter 114 may be coaxial with one another. For example, the outer sheath 112 and delivery catheter 114 may share a longitudinal axis 154 therethrough. In other embodiments, the outer sheath 112, delivery catheter 114, inner catheter 116, drive cable 118, or combinations thereof may be coaxial and/or share the longitudinal axis 154 of the elongated member 102. In another embodiment, outer sheath 112, delivery catheter 114, inner catheter 116, drive cable 118, or combinations thereof, may not be coaxial and/or share the longitudinal axis 154 of the elongated member 102. In at least one embodiment, the elongated member 102 may be an over-the-wire member and configured to have a guidewire 119 inserted through part of or all of the length of the elongated member 102. For example, the drive cable 118 may have a lumen therethrough that may allow a guidewire 119 to pass through a length of the drive cable 118 and/or elongated member 102.

A drive cable 118 may be a laterally flexible element with high torsional stiffness that is configured to transmit rotational force along a length thereof in a straight configuration and in a bent configuration.

In other embodiments, the drive cable 118 may be at least partially replaced by a cut hypotube. A cut hypotube may have flexibility in one or more lateral directions while transmitting torque therethrough with little to no rotation of a proximal end relative to a distal end.

In some embodiments, at least one of the outer sheath 112, delivery catheter 114, inner catheter 116, and drive cable 118 may be a steerable element. For example, at least one of the outer sheath 112, delivery catheter 114, inner catheter 116, and drive cable 118 may have a plurality of wires, threads, sutures, or chambers that may allow a lateral force to be applied to the element, as known in the art, to allow steerability of the elongated member 102. In at least one embodiment, the delivery catheter 114 may be a steerable catheter.

In at least one embodiment, a friction-reducing layer and/or coating may be located between the outer sheath 112 and the delivery catheter 114. For example, a friction-reducing layer and/or coating may include a polytetrafluoroethylene (PTFE) layer positioned between the outer sheath 112 and the delivery catheter 114. In other examples, other lubricious coatings, such as perfluoroalkoxy (PFA), fluorinated ethylene propylene, other fluoropolymers, other materials, or combinations thereof, may be applied between the elements of the elongated member 102 to reduce friction between the elements during longitudinal movement relative to one another.

In other embodiments, a friction-reducing layer and/or coating may be located between the drive cable 118 and the inner catheter 116, or other element radially surrounding the drive cable 118. The friction-reducing layer and/or coating may reduce rotation friction between the drive cable 118 and another element of the elongated member 102 when the drive cable 118 is rotated relative to the other element of the elongated member 102.

Figure 31:
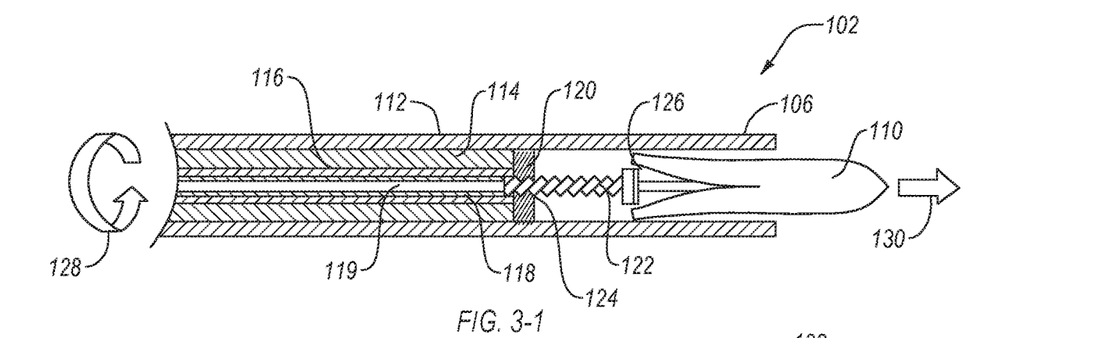
Figure 32:
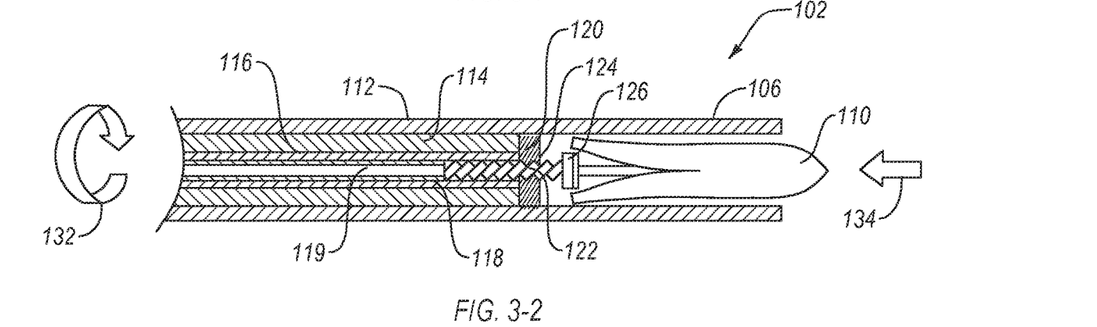

FIG. 3-1 and FIG. 3-2 are side cross-sectional views of an embodiment of the distal end 106 of the elongated member 102 described in relation to FIG. 2. In some embodiments, the distal end 106 may have an intravascular device 110 positioned therein and/or connected thereto. For example, the intravascular device 110 may be longitudinally adjacent a distal end cap 120. The distal end cap 120 may be longitudinally fixed to one or more elements of the elongated member 102. For example, the distal end cap 120 may be longitudinally fixed relative to the drive cable 118. In other examples, the distal end cap 120 may be longitudinally fixed relative to the delivery catheter 114 and/or inner catheter 116.

In some embodiments, the intravascular device 110 may be removably connected to the distal end cap 120. For example, the distal end cap 120 may have one or more retention features (e.g., threaded, pins, grooves, resilient clips, etc.) thereon and the intravascular device 110 may have one or more complimentary retention features thereon, such that the intravascular device 110 may selectively engage with the distal end cap 120. In other embodiments, the intravascular device 110 may abut the distal end cap 120 without interlocking, adhering, or otherwise connecting to the distal end cap 120.

The distal end 106 may have an outer sheath 112 at least partially longitudinally overlapping the intravascular device 110. In some embodiments, the intravascular device 110 may be an expandable device with a collapsed state and an expanded state. For example, the intravascular device 110 may be a MITRACLIP mitral valve repair device having one or more deployable clips that expand radially from a body of the repair device. The outer sheath 112 may protect the repair device and the patient's vasculature from one another during delivery and positioning of the device before deployment.

In other embodiments, the intravascular device 110 may be a self-expanding intravascular device 110 with a contracted state and an expanded state. The intravascular device 110 may be biased toward the expanded state such that the outer sheath 112 holds the intravascular device 110 in the contracted state, and a removal of the outer sheath 112 (e.g., moving the outer sheath 112 in a proximal direction) from a longitudinally overlapping position, such as shown in FIG. 3-1, may allow the expansion of the intravascular device 110 toward an expanded state. In some embodiments, the intravascular device 110 may include a shape memory material ("SMM") such as a shape memory polymer and/or a shape-memory metal. For example, the intravascular device 110 may include or be made of a nickel titanium alloy. In some embodiments, the intravascular device 110 in a contracted state may apply an expansive force to the outer sheath 112. The force experienced between the intravascular device 110 and the outer sheath 112 may create and/or increase a frictional force the outer sheath 112 and the intravascular device 110 and/or the delivery catheter 114.

In some embodiments, a longitudinal position of the intravascular device 110 may be at least partially controlled by a longitudinally moveable member within with the distal end 106 of the elongated member 102. Friction within the elongated member 102 and/or between the elongated member 102 and the patient's vasculature may inhibit and/or limit fine movements of the intravascular device 110 (i.e., due partially to elastic and/or plastic deformation along the length of the elongated member 102). To control the precise location of the intravascular device 110, a longitudinal force may be applied to the intravascular device 110 that originates locally to the distal end 106 of the elongated member 102. For example, after approximate placement of the distal end 106 of the elongated member 102 by overall movement of the elongated member 102 through the vasculature, a secondary positioning system in the elongated member 102 may provide fine adjustments to the position of the intravascular device 110. For example, FIG. 3-1 illustrates an embodiment of a secondary positioning system that may convert a rotation of the drive cable 118 to a longitudinal movement of the intravascular device 110.

In some embodiments, the drive cable 118 may be rotationally fixed relative to a threaded coil 122. The threaded coil 122 may be made of or include a coiled wire or other member that allows the threaded coil 122 to elastically deform during passage through the patient's vasculature. In some embodiments, the threaded coil 122 may be biased to a substantially straight orientation. In other embodiments, the threaded coil 122 may be shapeable to provide a shapeable distal end 106 to the elongated member 102. The threaded coil 122 may have a plurality of threads thereon, such that the threaded coil 122 may function as a screw gear, as will be described in more detail in relation to FIG. 5 through FIG. 12.

During delivery to and/or positioning of the intravascular device 110 at or near a target location in the patient's body, the intravascular device 110 may be at least partially or entirely radially within the outer sheath 112. Upon approximate positioning of the distal end 106 and the intravascular device 110 at or near the target location, a user may rotate the drive cable 118. The drive cable 118 may be rotationally fixed relative to the threaded coil 122. In some embodiments, the drive cable 118 may be welded to the threaded coil 122. In other embodiments, the drive cable 118 may be fixed relative to the threaded coil 122 by an adhesive or by a mechanical connection, such as interlocking features. In yet other embodiments, the drive cable 118 may be fixed relative to the threaded coil 122 by one or more intermediate elements, such as a pin, a staple, a clip, or other mechanical link between the drive cable 118 and the threaded coil 122.

The threaded coil 122 may engage with a complimentary thread 124 on the distal end cap 120 of the elongated member 102. The complimentary thread 124 may apply a longitudinal force to the threaded coil 122 upon rotation of the threaded coil 122. For example, FIG. 3-1 illustrates a clockwise rotation 128 (from a proximal perspective) of the drive cable 118. The rotation of the drive cable 118 is transmitted to the threaded coil 122 and the threaded coil 122 may rotate relative to the distal end cap 120. The threaded coil 122 may engage with the complimentary threads 124 of the distal end cap 120, which may, in turn, urge the threaded coil 122 in a distal direction 130. In other embodiments, the threaded coil 122 may engage with one or more complementary threads on the delivery catheter 114 and/or the inner catheter 116. The movement of the threaded coil 122 may urge the intravascular device 110 in a distal direction 130.

In some embodiments, the threaded coil 122 may be connected to the intravascular device 110. In other embodiments, the threaded coil 122 may be longitudinally fixed to the intravascular device 110 and rotationally independent from the intravascular device 110. For example, the threaded coil 122 may be connected to the intravascular device 110 with a rotational bearing 126, such that the threaded coil 122 and intravascular device 110 are rotationally independent. In some embodiments, the bearing 126 may be a ball bearing. In other embodiments, the bearing 126 may be a slide bearing. In yet other embodiments, the threaded coil 122 may be rotationally independent from the intravascular device 110, and the intravascular device 110 may be rotationally keyed to the outer sheath 112, distal end cap 120, or other element of the elongated member 102.

As shown in FIG. 3-2, the counter-clockwise rotation 132 (from a proximal perspective) of the drive cable 118 may be transmitted to the threaded coil 122. The threaded coil 122 may rotate relative to the distal end cap 120. The threaded coil 122 may engage with the complimentary threads 124 of the distal end cap 120, which may, in turn, urge the threaded coil 122 in a proximal direction 134. In other embodiments, the threaded coil 122 may engage with one or more complementary threads on the delivery catheter 114 and/or the inner catheter 116. The movement of the threaded coil 122 may urge the intravascular device 110 in a proximal direction 134.

Figure 41:
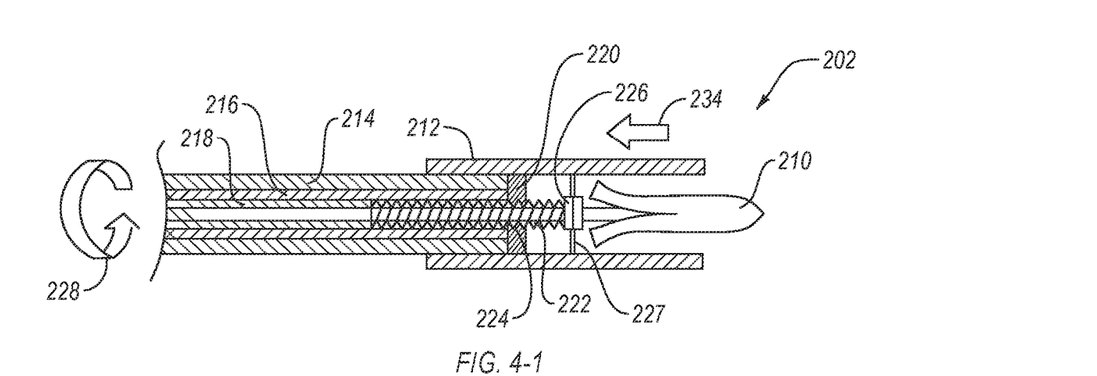

Referring now to FIG. 4-1, another embodiment of an elongated member 202 according to the present disclosure is shown. Rotation of a drive cable 218 coupled to a threaded coil 222 in a clockwise direction 228 may cause the threaded coil 222 to engage with complimentary threads 224 and move the threaded coil 222 longitudinally. The threaded coil 222 may apply a longitudinal force to and move an outer sheath 212 or other element of the elongated member 202 in the proximal direction 234. The outer sheath 212 or other element of the elongated member 202 may move relative to the delivery catheter 214, inner catheter 216, distal end cap 220, or combinations thereof. In at least one embodiment, the outer sheath 212 or other element of the elongated member 202 may move longitudinally relative to the intravascular device 210.

The outer sheath 212 may be shortened to longitudinally overlap the intravascular device 210 and a portion of the delivery catheter 214. In other embodiments, the outer sheath 212 may extend from a proximal end of the elongated member 202 to the distal end of the elongated member 202, such as in the elongated member 102 described in relation to FIG. 1 and FIG. 2.

Referring again to FIG. 4-1, in some embodiments, the threaded coil 222 may be longitudinally fixed relative to the outer sheath 212 by a distal connection member 227. The distal connection member 227 may be continuous between the threaded coil 222 and the outer sheath 212 (i.e., a continuous disc). In other embodiments, the distal connection member 227 may be one or more struts or other radial connection members that connect the threaded coil 222 and the outer sheath 212.

In some embodiments, the distal connection member 227 that connects the threaded coil 222 to the outer sheath 212 may be connected to a bearing 226. The distal connection member 227 may be rotationally independent of the threaded coil 222 and located between the bearing 226 and the outer sheath 212. In other embodiments, the distal connection member 227 may be rotationally fixed relative to the threaded coil 222 and a bearing 226 may be located between the distal connection member 227 and the outer sheath 212. In yet other embodiments, the outer sheath 212 and distal connection member 227 may be both rotationally fixed relative to the threaded coil 222.

In self-expanding embodiments, the intravascular device 210 may expand radially outward beyond the outer sheath 212 upon proximal movement of the outer sheath 212 relative to the intravascular device 210. In embodiments with one or more retention features on the distal end cap 220 and the intravascular device 210, the longitudinal position of the intravascular device 210 relative to the distal end cap 220 may be fixed. For example, after a partial expansion of the intravascular device 210, the intravascular device 210 may be urged back to a contracted state.

Figure 42:
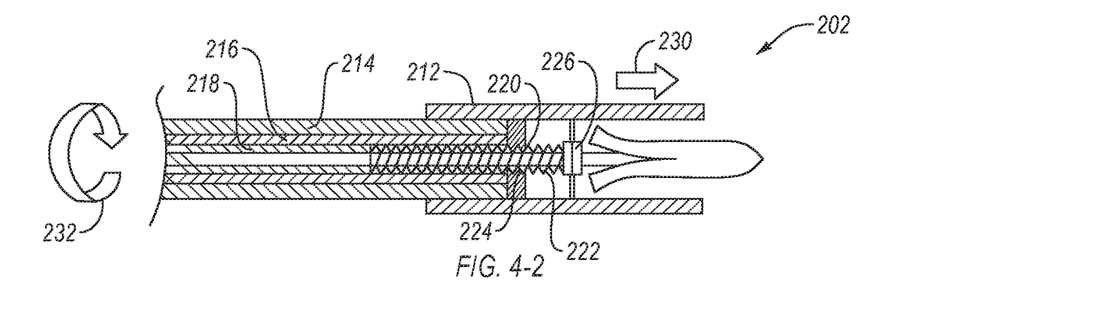

As shown in FIG. 4-2, the counter-clockwise rotation 232 (opposite that in FIG. 4-1) of the drive cable 218 may be transmitted to the threaded coil 222. The rotation may cause the threaded coil 222 to engage with complimentary threads 224 and move the threaded coil 222 longitudinally. The threaded coil 222 may apply a longitudinal force to and move an outer sheath 212 or other element of the elongated member 202 in the distal direction 230. The outer sheath 212 or other element of the elongated member 202 may move relative to the delivery catheter 214, inner catheter 216, distal end cap 220, or combinations thereof. In at least one embodiment, the outer sheath 212 or other element of the elongated member 202 may move longitudinally relative to the intravascular device 210.

In some embodiments, the bearing 226 may be a one-way bearing, allowing rotation in a first direction and resisting rotation in a second direction. A one-way bearing may be used to allow only deployment of an intravascular device, if recapture or other proximal movement of the intravascular device is undesirable.

While the depicted embodiments in FIG. 3-1 through FIG. 4-2 illustrate the threaded coil engaging with a complimentary thread on the distal end cap, it should be understood that the threaded coil may engage with a complimentary thread on the distal connection member, intravascular device, or other component of the intravascular device delivery system. For example, the threaded coil may be longitudinally fixed by a bearing relative to the distal end cap, the threaded coil may engage with a complimentary thread on the intravascular device. In other words, the threaded coil may rotate while remaining in the same longitudinal position relative to the distal end cap, and the rotation of the threaded coil may urge the intravascular device proximally or distally. In another example, the threaded coil may rotate while remaining in the same longitudinal position relative to the distal end cap, and the rotation of the threaded coil may urge the outer sheath proximally or distally.

In some embodiments, a threaded coil may include a plurality of coils helixed together, such as embodiments described in relation to FIG. 5 through FIG. 9. In other embodiments, a threaded coil may include a single coil. For example, the single coil may be a shaped coil to create threads, which engage with complimentary threads on the distal end cap.

Figure 5:
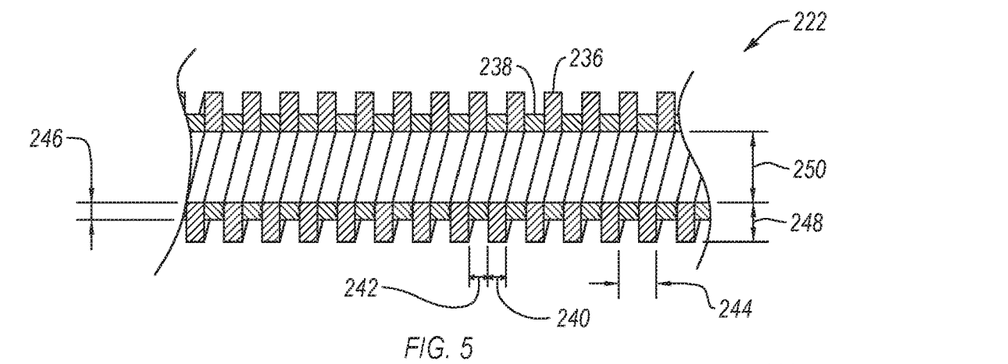
FIG. 5 is a side cross-sectional view of the embodiment of a threaded coil of FIG. 4-1, according to the present disclosure.

FIG. 5 is a perspective cutaway view of an embodiment of a threaded coil 222 according to the present disclosure. The threaded coil 222 may include a major coil 236 and a minor coil 238 that may be helixed together (i.e., interlocked spiral coils) to create a substantially continuous spiral coil. The major coil 236 and minor coil 238 may have different radial widths, such that the major coil 236 projects radially outward farther than the minor coil 238, creating a spiral recess in the threaded coil 222 that may act as a thread to engage with a complimentary thread and transfer forces.

In some embodiments, the major coil 236 may have a major coil length 240 in the longitudinal direction. Similarly, the minor coil 238 may have a minor coil length 242 in the longitudinal direction. In some embodiments, the major coil length 240 and/or the minor coil length 242 may be constant along a length of the threaded coil 222. In other embodiments, the major coil length 240 and/or the minor coil length 242 may vary along a length of the threaded coil 222. For example, lateral flexibility at a distal end of the threaded coil 222 may be increased or altered by decreasing the major coil length 240 and/or minor coil length 242 closer to the distal end of the threaded coil 222.

In some embodiments, the major coil length 240 and the minor coil length 242 may be substantially equal. For example, the major coil length 240 and the minor coil length 242 may both be about 1 millimeter. In other embodiments, the major coil length 240 may be greater than the minor coil length 242. For example, the major coil length 240 may be about 1.0 millimeter and the minor coil length 242 may be less than 1.0 millimeter. In yet other embodiments, the major coil length 240 may be less than the minor coil length 242. For example, the major coil length 240 may be about 1.0 millimeter and the minor coil length 242 may be more than 1.0 millimeter.

In some embodiments, the threaded coil 222 may be tightly packed such that the major coil 236 and minor coil 238 abut one another along at least a length of the threaded coil 222. Alternatively, in another embodiment, the distal end and/or proximal ends of threaded coil 222 are tightly packed such that major coil 236 and minor coil 238 abut one another. In another embodiment, at the distal end and/or proximal end of the coil 222 the minor coil 238 is tightly packed. Such an arrangement of the distal and/or proximal end of a coil may enhance the ability to attach the proximal end or the distal end of the coil to other elements of the delivery device by such methods as welding, brazing, adhesives or other fixation methods.

In other embodiments, the threaded coil 222 may be tightly packed such that the major coil 236 and minor coil 238 abut one another along the entire length of the threaded coil 222. In yet other embodiments, the threaded coil 222 may be loosely packed, such that there is a space between the major coil 236 and the minor coil 238 in the longitudinal direction. For example, in an embodiment that is tightly packed, such as that shown in FIG. 5, the major coil length 240 and the minor coil length 242 may be substantially equal to the pitch 244. In other examples, such as a loosely packed embodiment, the pitch 244 may be greater than the sum of the major coil length 240 and the minor coil length 242.

In some embodiments, the major coil 236 and the minor coil 238 may define a lumen therethrough with a lumen diameter 250. The lumen diameter 250 may be sized to permit a guidewire or other elongated element to extend at least partially through the threaded coil 222. In some embodiments, the lumen diameter 250 may be in a range having an upper value, a lower value, or an upper and lower value including any of 0.025 inches, 0.030 inches, 0.035 inches, 0.040 inches, 0.045 inches, 0.050 inches, 0.060 inches, 0.070 inches, 0.080 inches, 0.090 inches, 0.100 inches, or any values therebetween. For example, the lumen diameter 250 may be greater than 0.025 inches. In another example, the lumen diameter 250 may be less than 0.100 inches. In other examples, the lumen diameter 250 may be in a range of 0.025 inches to 0.100 inches. In at least one example, the lumen diameter 250 may be about 0.035 inches.

The minor coil 238 has a minor coil height 246 that is a radial distance from an inner surface (i.e., the surface that partially defines the lumen) of the minor coil 238 and an outer surface of the minor coil 238. The major coil 236 has a major coil height 248 that is a radial distance from an inner surface (i.e., the surface that partially defines the lumen) of the major coil 236 and an outer surface of the major coil 236. The difference between the minor coil height 246 and the major coil height 248 may partially define a thread depth of the threaded coil 222. In some embodiments, a thread depth may be in a range having an upper value, a lower value, or an upper and lower value including any of 0.005 inches, 0.010 inches, 0.015 inches, 0.020 inches, 0.025 inches, 0.030 inches, 0.035 inches, 0.040 inches. In some examples, the thread depth is greater than 0.005 inches. In other examples, the thread depth is less than 0.040 inches. In yet other examples, the thread depth is between 0.005 inches and 0.040 inches.

Figure 6:
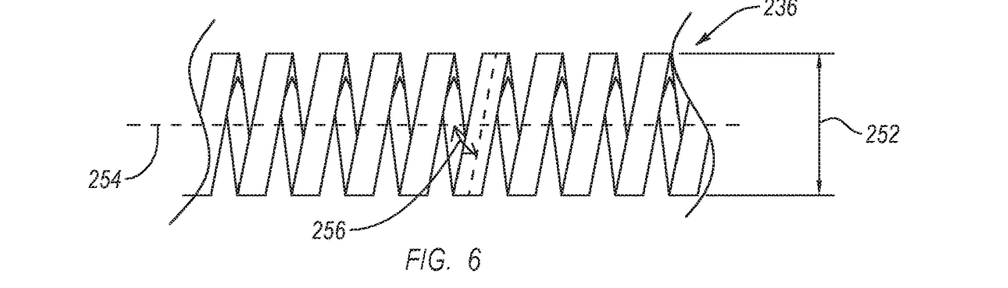
FIG. 6 is a side view of the embodiment of a major coil of the threaded coil of FIG. 5, according to the present disclosure.

FIG. 6 is a side view of the embodiment of the major coil 236 of FIG. 5. The major coil 236 may have a major coil outer diameter 252 that is perpendicular to a longitudinal axis 254 of the major coil 236 (and, hence, the threaded coil). In some embodiments, the major coil outer diameter 252 may be in a range having an upper value, a lower value, or an upper and lower value including any of 0.030 inches, 0.035 inches, 0.040 inches, 0.045 inches, 0.050 inches, 0.055 inches, 0.060 inches, 0.065 inches, 0.070 inches, 0.075 inches, 0.080 inches, 0.085 inches, 0.090 inches, 0.095 inches, 0.100 inches, 0.105 inches, or any values therebetween. For example, the major coil outer diameter 252 may be greater than 0.030 inches. In another example, the major coil outer diameter 252 may be less than 0.105 inches. In other examples, the major coil outer diameter 252 may be in a range of 0.030 inches to 0.105 inches. In at least one example, the major coil outer diameter 252 may be about 0.045 inches.

The major coil 236 may have a plurality of coils angled relative to the longitudinal axis 254 at a coil angle 256. In some embodiments, the pitch of the threaded coil may be at least partially related to the coil angle 256. The coil angle 256 may be the angle of the coil as the coil crosses the longitudinal axis 254, viewed radially (i.e., perpendicular to the longitudinal axis in the radial direction). In some embodiments, the coil angle 256 may be in a range having an upper value, a lower value, or an upper and lower value including any of 45°, 50°, 55°, 60°, 65°, 70°, 75°, 80°, 85°, 87°, 89°, or any value therebetween. For example, the coil angle 256 may be greater than 45°. In another example, the coil angle 256 may be less than 89°. In other examples, the coil angle 256 may be between 45° and 89°. In at least one example, the coil angle 256 may be about 75°.

Figure 7:
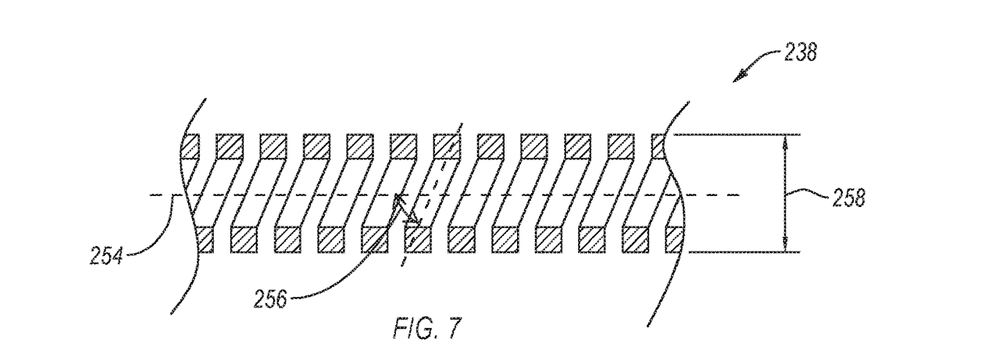
FIG. 7 is a side cross-sectional view of the embodiment of a minor coil of the threaded coil of FIG. 5, according to the present disclosure.

FIG. 7 illustrates the embodiment of a minor coil 238 of FIG. 5 in side cross-sectional view. The minor coil 238 may have a minor coil outer diameter 258 that is perpendicular to a longitudinal axis 254 of the minor coil 238 (and, hence, the threaded coil). In some embodiments, the minor coil outer diameter 258 may be in a range having an upper value, a lower value, or an upper and lower value including any of 0.025 inches, 0.030 inches, 0.035 inches, 0.040 inches, 0.045 inches, 0.050 inches, 0.055 inches, 0.060 inches, 0.065 inches, 0.070 inches, 0.075 inches, 0.080 inches, 0.085 inches, 0.090 inches, 0.095 inches, 0.100 inches, or any values therebetween. For example, the minor coil outer diameter 258 may be greater than 0.025 inches. In another example, the minor coil outer diameter 258 may be less than 0.100 inches. In other examples, the minor coil outer diameter 258 may be in a range of 0.025 inches to 0.100 inches. In at least one example, the minor coil outer diameter 258 may be about 0.078 inches.

The minor coil 238 may have a plurality of coils angled relative to the longitudinal axis 254 at the coil angle 256. The coil angle 256 is the same between the major coil 236 and the minor coil 238 in order to helix the major coil 236 and minor coil 238 together.

Figure 8:
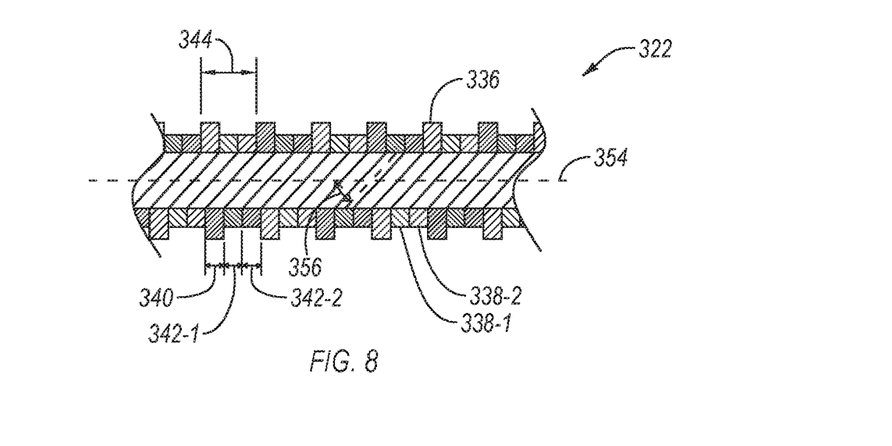
FIG. 8 is a side cross-sectional view of another embodiment of a threaded coil, according to the present disclosure.

In some embodiments, a threaded coil may have a plurality of major coils and/or a plurality of minor coils. FIG. 8 illustrates another embodiment of a threaded coil 322, according to the present disclosure. The threaded coil 322 has a major coil 336 and a plurality of minor coils 338-1, 338-2 helixed together. The major coil 336 may have a major coil length 340, such as described in relation to FIG. 5. The first minor coil 338-1 may have a first minor coil length 342-1 and the second minor coil 338-2 may have a second minor coil length 342-2. In some embodiments, the first minor coil length 342-1 and the second minor coil length 342-2 may be substantially equal. In other embodiments, the first minor coil length 342-1 may be greater than the second minor coil length 342-2. In other embodiments, the first minor coil length 342-1 may be less than the second minor coil length 342-2.

The pitch 344 of the threaded coil 322, therefore, may be a longitudinal length between the major coil 336 projections with both the first minor coil 338-1 and the second minor coil 338-2 therebetween. In some embodiments, the threaded coil 322 may be tightly packed with a pitch 344 that is substantially equal to the sum of the major coil length 340, the first minor coil length 342-1, and the second minor coil length 342-2, similar to as described in relation to FIG. 5. In other embodiments, the threaded coil 322 may be loosely packed with a pitch 344 greater than the sum of the major coil length 340, the first minor coil length 342-1, and the second minor coil length 342-2, similar to as described herein.

In other embodiments, a threaded coil 322 may have a plurality of major coils 336. For example, the plurality of major coils 336 may be adjacent one another, such as the minor coils 338-1, 338-2 of FIG. 8. In another example, the plurality of major coils 336 may be spaced apart from on another by one or more minor coils, and may provide a double thread for the threaded coil 322, such as shown in FIG. 8.

In some embodiments, a coil angle 356 of the threaded coil 322 relative to the longitudinal axis 354 may be constant along a length of the threaded coil 322. In other embodiments, the coil angle 356 may vary along a length of the threaded coil 322 to alter the flexibility of the threaded coil 322. In yet other embodiments, the coil angle 356 may be constant along the entire length of the threaded coil 322.

Figure 9:
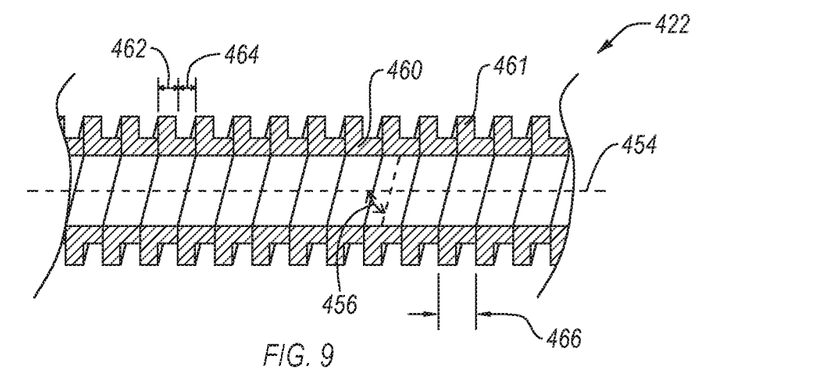
FIG. 9 is a side cross-sectional view of an embodiment of a threaded coil having a shaped wire, according to the present disclosure.

FIG. 9 illustrates yet another embodiment of a threaded coil 422. In some embodiments, the threaded coil 422 may include a shaped wire coil 460. The shaped wire coil 460 may be formed in a spiral coil wherein the shaped wire coil 460 has a radially outward projection 461 that extends away from the longitudinal axis 454 of the threaded coil 422. The projection 461 may have one or more dimensions similar to the major coil described in FIG. 5. In some embodiments, the projection 461 may have a projection length 462 in the longitudinal direction.

While the shaped wire coil 460 is depicted in FIG. 9 as having a substantially L-shaped cross-section, other embodiments of a shaped wire coil may have other shapes in cross-section. For example, other embodiments may have an inverted T-shaped cross-section, a U-shaped cross-section, or other shapes in cross-section.

The shaped wire coil 460 may have a recessed portion that is radially closer to the longitudinal axis 454 than the projections 461. The recessed portion of the shaped wire coil 460 may have one or more dimensions similar to the minor coil described in FIG. 5. The recessed portion may define a recessed length 464 of the shaped wire coil 460. In some embodiments, such as that shown in FIG. 9, the projection length 462 and the recessed length 464 may be substantially equal. In other embodiments, the projection length 462 may be greater than the recessed length 464. In yet other embodiments, the projection length 462 may be less than the recessed length 464. In some embodiments, a pitch 466 of the threaded coil 422 may be based upon the shaped wire coil 460. In other embodiments, a shaped wire coil may be helixed with one or more major coils and/or minor coils to create a threaded coil having a different pitch than the shaped wire coil 460 alone.

In some embodiments, a coil angle 456 of the threaded coil 422 relative to the longitudinal axis 454 may be constant along a length of the threaded coil 422. In other embodiments, the coil angle 456 may vary along a length of the threaded coil 422 to alter the flexibility of the threaded coil 422. In yet other embodiments, the coil angle 456 may be constant along the entire length of the threaded coil 422.

Figure 10:
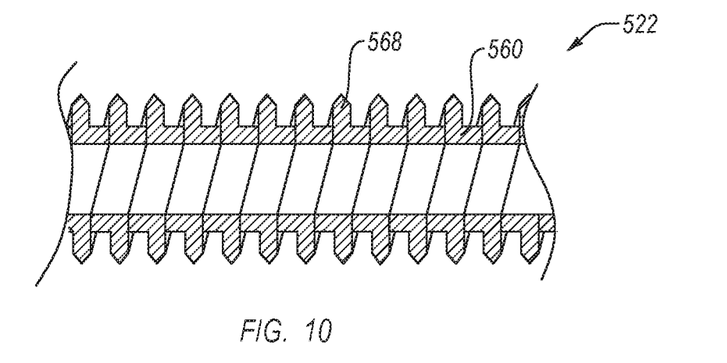
FIG. 10 is a side cross-sectional view of an embodiment of a threaded coil having tapered threads, according to the present disclosure.

FIG. 10 illustrates another embodiment of a threaded coil 522. The threaded coil 522 may be a shaped wire coil 560 similar to that described in relation to FIG. 9. The threaded coil 522 may have a peaked tip 568 at a radially outermost portion of the threaded coil 522. The peaked tip 568 of the threaded coil 522 may allow for a snug fit in the complimentary threads of the distal end cap or other structure, as described herein. In some embodiments, the peaked tip 568 may reduce rotational friction. In other embodiments, the peaked tip 568 may inhibit fluid flow between the threaded coil 522 and the complimentary threads. While FIG. 10 illustrates a shaped wire coil 560 with a peaked tip 568, the peaked tip 568 may be used in conjunction with other embodiments of threaded coils, such as with the major coil 236 described in relation to FIG. 5 or the plurality of major coils 336 described in relation to FIG. 8.

Figure 11:
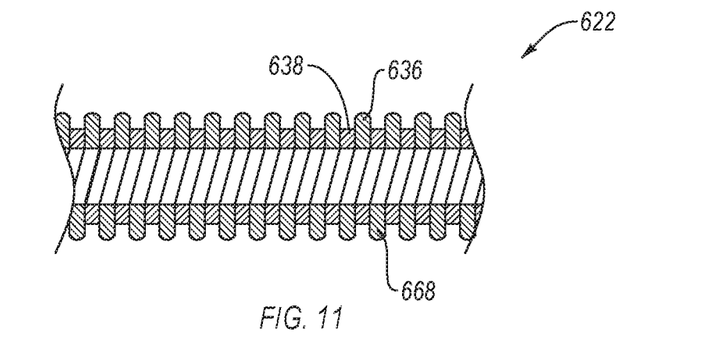
FIG. 11 is a side cross-sectional view of another embodiment of a threaded coil having rounded threads, according to the present disclosure.

FIG. 11 illustrates yet another embodiment of a threaded coil 622. The threaded coil 622 may include at least one major coil 636 and at least one minor coil 638 similar to that described in relation to FIG. 5. The threaded coil 622 may have a rounded tip 668 at a radially outermost portion of the threaded coil 622. The rounded tip 668 of the threaded coil 622 may allow for a snug fit in the complimentary threads of the distal end cap or other structure, as described herein. In some embodiments, the rounded tip 668 may reduce rotational friction. In other embodiments, the rounded tip 668 may compress against a surface of complimentary threads and the resulting seal may inhibit fluid flow between the threaded coil 622 and the complimentary threads. While FIG. 11 illustrates a major coil 636 with a rounded tip 668, the rounded tip 668 may be used in conjunction with other embodiments of threaded coils, such as with the plurality of major coils 336 described in relation to FIG. 8 or with the shaped wire coil 460 described in relation to FIG. 9.

Figure 12:
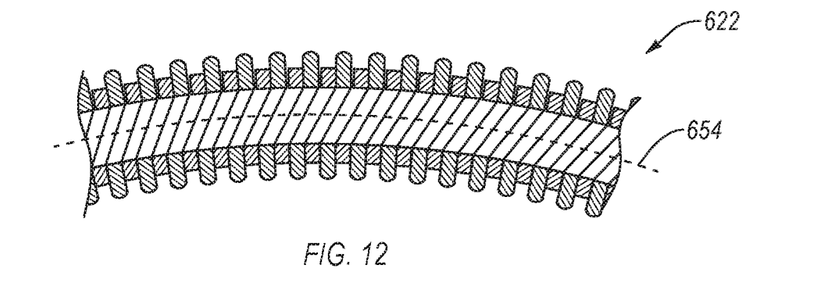
FIG. 12 is a side cross-sectional view of an embodiment of a threaded coil flexing under a lateral force, according to the present disclosure.

FIG. 12 is a side cross-sectional view of the embodiment of a threaded coil 622, described in FIG. 11, flexing in a lateral direction, such that the longitudinal axis 654 is curved. As shown in FIG. 12, the threaded coil 622 may flex one or more components of the threaded coil 622 (e.g., a major coil, a minor coil, a shaped wire coil) elastically deforming and/or moving relative to one another. In some embodiments, the threaded coil 622 may include or be made of a SMM, such as a shape memory polymer and/or a shape-memory metal. For example, a threaded coil may include or be made of a nickel titanium alloy. In other embodiments, a threaded coil may include or be made of other materials that exhibit elastic deformation, such as steel, titanium alloys, aluminum alloys, polymers, ceramics, or other materials that may flex under a lateral load and return to an original state.

Figure 13:
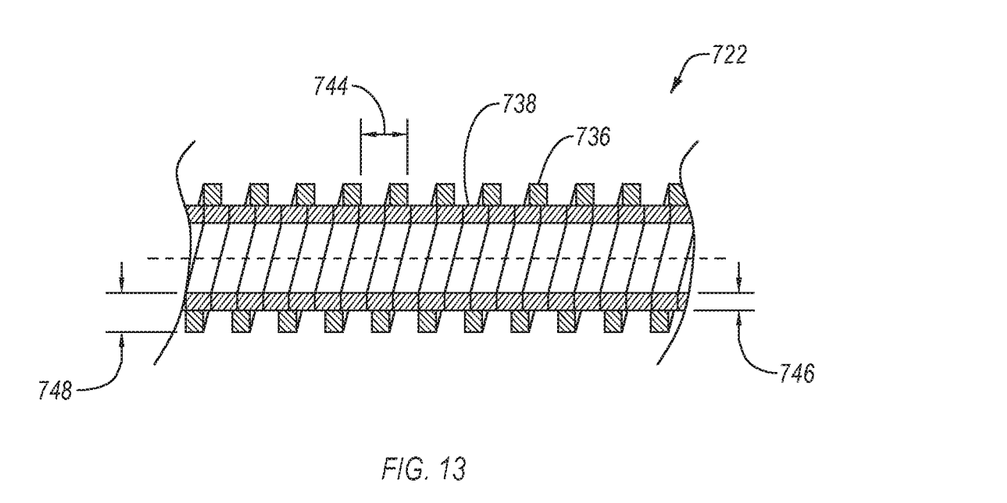
FIG. 13 is a side cross-sectional view of yet another embodiment of a threaded coil, according to the present disclosure.

FIG. 13 illustrates a cross-sectional view of yet another embodiment of a threaded coil 722 according to the present disclosure. The threaded coil 722 may have a major coil 736 that is wrapped around an outer surface of a minor coil 738. For example, the minor coil 738 may be radially within the inner surface of the major coil 736. In some embodiments, the major coil 736 may be fixed relative to the minor coil 738, such as by welding, brazing, adhesives, or other fixation methods. For example, the major coil 736 may be fixed to the minor coil 738 along a continuous longitudinal length of the major coil 736. In other examples, the major coil 736 may be fixed to the minor coil 738 at one or more discontinuous locations along the longitudinal length of the major coil 736 (e.g., spot welded to the minor coil 738).

In some embodiments, the pitch 744 may be determined by the major coil 736 independently of the minor coil 738. In some embodiments, the minor coil 738 has a minor coil height 746 that is a radial distance from an inner surface (i.e., the surface that partially defines the lumen) of the minor coil 738 and an outer surface of the minor coil 738. The major coil 736 has a major coil height 748 that is a radial distance from an inner surface (i.e., the surface that partially defines the lumen) of the minor coil 738 and an outer surface of the major coil 736. The difference between the minor coil height 746 and the major coil height 748 may partially define a thread depth of the threaded coil 722.

Figure 14:
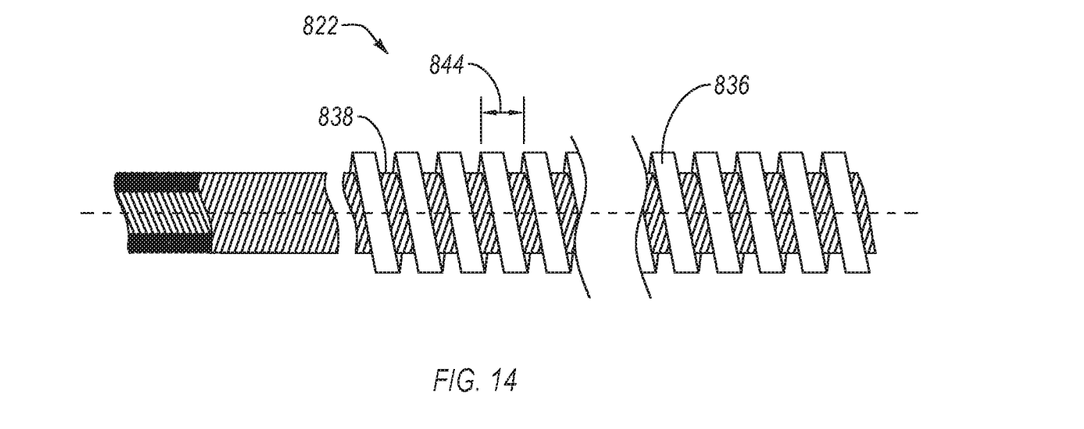
FIG. 14 is a side partial cross-sectional view of a further embodiment of a threaded coil, according to the present disclosure.

FIG. 14 illustrates a partial cross-sectional view of a further embodiment a threaded coil 822 according to the present disclosure. In some embodiments, the minor coil 838 may be a cable tube or a braided tube. As shown in FIG. 14, the threaded coil 822 may have a major coil 836 that is wrapped around an outer surface of a cable tube minor coil 838 that is made up of a plurality of wrapped and/or braided wires. In some embodiments, the major coil 836 may be fixed relative to a radially outer surface of the cable tube minor coil 838, such as by welding, brazing, adhesives, or other fixation methods. As the cable tube minor coil 838 does not have a defined pitch, the pitch 844 of the threaded coil 822 may be defined by the pitch of the major coil 836.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. A threaded device, the device comprising:
   a first elastically deformable wire and a second elastically deformable wire spiraled about a longitudinal axis, the first elastically deformable wire and the second elastically deformable wire defining a lumen therethrough that is adapted to receive a guidewire, the first elastically deformable wire and the second elastically deformable wire being spirally interlocked to form a continuous coil including at least one thread on a radially outer surface of the coil, the thread being formed from at least a portion of each of the first elastically deformable wire and the second elastically deformable wire.

2. The device of claim 1, wherein the first elastically deformable wire has a projection and a recessed portion, the projection defining the thread on the radially outer surface.

3. The device of claim 1, wherein the first elastically deformable wire is a major coil and the second elastically deformable wire is a minor coil.

4. The device of claim 3, wherein the major coil has a major coil length and the minor coil has a minor coil length, a pitch of the thread being a sum of the major coil length and the minor coil length.

5. The device of claim 3, wherein the major coil has a major coil outer diameter in a range of 0.030 inches to 0.105 inches.

6. The device of claim 1, wherein the lumen has a lumen diameter in a range of 0.025 inches to 0.100 inches.

7. The device of claim 1, wherein the at least one of the first elastically deformable wire and the second elastically deformable wire includes a shape memory material.

8. An intravascular device delivery system, the system comprising:
   an elongated member having a proximal end, a distal end, and a longitudinal axis therebetween;
   a threaded coil positioned near the distal end of the elongated member, the threaded coil comprising:
      a first elastically deformable wire and a second elastically deformable wire spiraled about a longitudinal axis, the first elastically deformable wire and the second elastically deformable wire defining a lumen therethrough that is adapted to receive a guidewire, the first elastically deformable wire and the second elastically deformable wire being spirally interlocked to form a continuous coil including at least one thread on a radially outer surface of the continuous coil, the thread being formed from at least a portion of each of the first elastically deformable wire and the second elastically deformable wire; and
   a drive cable positioned in the elongated member and extending from the proximal end to the threaded coil, the drive cable being rotationally fixed relative to the threaded coil and comprising a lumen that is adapted to receive the guidewire.

9. The system of claim 8, wherein the elongated member includes an outer sheath and the threaded coil is longitudinally fixed relative to the outer sheath.

10. The system of claim 8, further comprising a bearing connected to a distal end of the threaded coil.

11. The system of claim 8, further comprising a distal end cap having complimentary threads configured to engage with the at least one thread of the threaded coil.

12. A method of delivering an intravascular device, the method comprising:
   inserting an elongated member containing a threaded coil and a distal end cap into a patient's vasculature;
   applying a rotational force to the threaded coil;
   engaging a thread of the threaded coil with a complimentary thread of the distal end cap; and
   rotating the threaded coil to apply a longitudinal force between the complimentary thread and the threaded coil to longitudinally reposition an intravascular device releasably mounted to a distal end of the threaded coil with respect to the distal end cap, a proximal end of the intravascular device being releasably mounted to the distal end of the threaded coil.

13. The method of claim 12, wherein inserting the elongated member includes elastically deforming the threaded coil.

14. The method of claim 12, wherein longitudinally repositioning the intravascular device comprises moving an outer sheath of the elongated member in the proximal direction relative to the threaded coil.

15. The method of claim 12, wherein longitudinally repositioning the intravascular device comprises moving the outer sheath relative to the distal end cap.

16. The method of claim 12, further comprising moving the threaded coil longitudinally.

17. The method of claim 12, wherein longitudinally repositioning the intravascular device comprises moving a bearing mounted to an outer sheath to expose the intravascular device.

18. The method of claim 12, wherein longitudinally repositioning the intravascular device comprises distally advancing the intravascular device from a distal end of an outer sheath.

* * * * *